United States Patent
Kandarian

(10) Patent No.: US 9,566,139 B2
(45) Date of Patent: Feb. 14, 2017

(54) STABILIZER FOR LOWER DENTAL APPLIANCES

(71) Applicant: Ronald Brent Kandarian, Kalispell, MT (US)

(72) Inventor: Ronald Brent Kandarian, Kalispell, MT (US)

(*) Notice: Subject to any disclaimer, the term of this patent is extended or adjusted under 35 U.S.C. 154(b) by 0 days.

(21) Appl. No.: 14/288,029

(22) Filed: May 27, 2014

(65) Prior Publication Data

US 2014/0363786 A1 Dec. 11, 2014

Related U.S. Application Data

(60) Provisional application No. 61/831,621, filed on Jun. 6, 2013.

(51) Int. Cl.
*A61C 13/225* (2006.01)
*A61C 13/12* (2006.01)

(52) U.S. Cl.
CPC .................... *A61C 13/225* (2013.01)

(58) Field of Classification Search
CPC . A61C 13/00; A61C 13/0025; A61C 13/0003; A61C 13/0001; A61C 13/26; A61C 13/01; A61C 13/0024; A61C 13/10; A61C 13/0006
USPC .............. 433/167–176, 177, 180; 264/16–17
See application file for complete search history.

(56) References Cited

U.S. PATENT DOCUMENTS

| | | | | |
|---|---|---|---|---|
| 3,023,499 A | * | 3/1962 | Michaelides | A61C 13/225 433/172 |
| 4,812,121 A | * | 3/1989 | Winder | A61C 13/24 433/172 |
| 5,431,563 A | * | 7/1995 | Huybrechts | A42B 3/12 128/862 |
| 2006/0040234 A1 | * | 2/2006 | Posca | A61C 13/2255 433/177 |
| 2007/0106138 A1 | * | 5/2007 | Beiski | A61B 5/682 600/349 |
| 2008/0299517 A1 | * | 12/2008 | Delaney, II | A61C 13/245 433/185 |

* cited by examiner

*Primary Examiner* — Matthew Nelson
(74) *Attorney, Agent, or Firm* — Michael B. Dodd; Dodd Law Group, LLC

(57) ABSTRACT

The present invention extends to a dental appliance having a set of rigid flanges conforming to a patient's mandibular bone structure and a stabilizer for securing and resisting movement of the dental appliance once set. The stabilizer reduces movement of a lower denture. The stabilizer extends perpendicularly from a flange of the lower denture and reduces denture movement during chewing. The stabilizer has one surface making contact with the bottom of the tongue and another surface making contact with the Genioglossus muscle when a user is chewing. The stabilizer does not require a dental implant for maintaining lower denture stability.

11 Claims, 4 Drawing Sheets

STABILIZER FOR LOWER DENTAL APPLIANCES

CROSS-REFERENCE TO RELATED APPLICATIONS

This application claims the benefit of and priority to U.S. Provisional Application No. 61/831,621, entitled "Stabilizer for Lower Dental Appliances," and filed on Jun. 6, 2013, which is incorporated herein by reference.

BACKGROUND

1. Field of the Invention

The present invention relates generally to devices for retaining and stabilizing mandibular (lower) dental appliances. More particularly, the present invention relates to the inclusion of one or more stabilizers placed in an appropriate area on a mandibular denture or partial denture with either lateral or bi-lateral distal extensions; thus increasing stabilization and security for greater masticatory (chewing) ability, stability and comfort.

2. Related Art

Lower dentures present an accepted problem for both the wearer and the dental provider—those problems are related to looseness and movement. There have been numerous attempts to overcome this dilemma by a variety of protocols; all of which did little to resolve the condition; and in some cases exacerbated it.

Today, the accepted protocol to overcome this problem is the placement of implant abutments. Implant abutments are mechanical devices consisting of a male and a female counterpart. The male portion must be surgically inserted through the periosteum (tissue covering the bone surface) and then into the osseous (bone) portion of the mandible. This technique requires anywhere from 2-4 or even more implants and typically costs multiple thousands of dollars. Further, the implants can fail because of the patient's biologic or physiologic rejection of the devices or due to poor placement causing breakdown of the supportive osseous (bone) hard tissue. Additionally, the patient is required to maintain more dentist visits so the dentist can monitor the health of the tissues supporting the implants causing additional expenses to the patient.

Further, conventional dentures or the like, especially mandibular and distal extension partial dentures are predominantly designed to be placed over the gums, and generally rely on gravity, tooth clasps, and/or adhesives to retain them in place. Various denture retaining devices are available in the prior art, but have up to now met with limited success. For example, some techniques use three piece lower dentures wherein two side pieces extend lower than a middle piece. Upon placement in the mouth, the pieces are attached together through interlocking tongue and groove or other construction which allow movement in a vertical direction. Besides the relative difficulty in maneuvering the three pieces in the user's mouth, any sufficient force on the central piece of these dentures from the incisor load may not be effectively transferred to the side pieces. This may lead to shear separation of the connections between the central piece and side pieces.

Other techniques use a device for retaining a lower denture having an externally fixed element, a retaining tongue which slides within a fixed element, and a cover piece which covers the fixed element and a portion of the retaining tongue. To use this device, the fixed element is secured to a lower denture such that the retaining tongue slides downward. After placement in the mouth, the user must slide the tongue below the mylohyoid ridge, and then place the cover piece to secure the retaining tongue in position. Besides the necessity for complex user manipulation, this device applies pressure to the cavity below the mylohyoid ridge on a relatively small surface area. Further, the protruding structure of this device may lead to irritation and abrasion, thereby reducing the comfort with which the attached denture may be worn.

Further techniques, use flexible dentures which grip the gums of users. However, these dentures do not extend below the mylohyoid ridge or any other like bone ridges to provide support.

Additional techniques appear to be spring loaded and spanning the length of the flange extension and embedded within said flange extension. The material providing the hinged action expresses a rigid flanged denture with a hinged portion to fit into the natural undercuts of the mylohyoid ridge.

BRIEF SUMMARY

The present invention extends to a dental appliance having a set of rigid flanges conforming to a patient's mandibular bone structure and a stabilizer for securing and resisting movement of the dental appliance once set. Embodiments of the invention include stabilizers for lower dental appliances. A lower dental appliance includes a rigid distal flange that is fixed to and extends essentially perpendicular from a rigid lingual flange of the denture. The rigid distal flange acts as a control surface. The rigid distal flange is dimensioned and configured so that one surface contacts the superior (top) aspect of the Genioglossus muscle. The rigid distal flange is also dimensioned and configured so that another surface contacts the inferior/lateral (bottom)/(side) area of the tongue.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION

The present invention extends to a dental appliance having a set of rigid flanges conforming to a patient's mandibular bone structure and a stabilizer for securing and resisting movement of the dental appliance once set. Embodiments of the invention include stabilizers for lower dental appliances. A lower dental appliance includes a rigid distal flange that is fixed to and extends essentially perpendicular from a rigid lingual flange of the denture. The rigid distal flange acts as a control surface. The rigid distal flange is dimensioned and configured so that one surface contacts the superior (top) aspect of the Genioglossus muscle. The rigid distal flange is also dimensioned and configured so that another surface contacts the inferior/lateral (bottom)/(side) area of the tongue.

In this specification and the following claims a dental appliance may be referred to as a denture.

Figure 1:
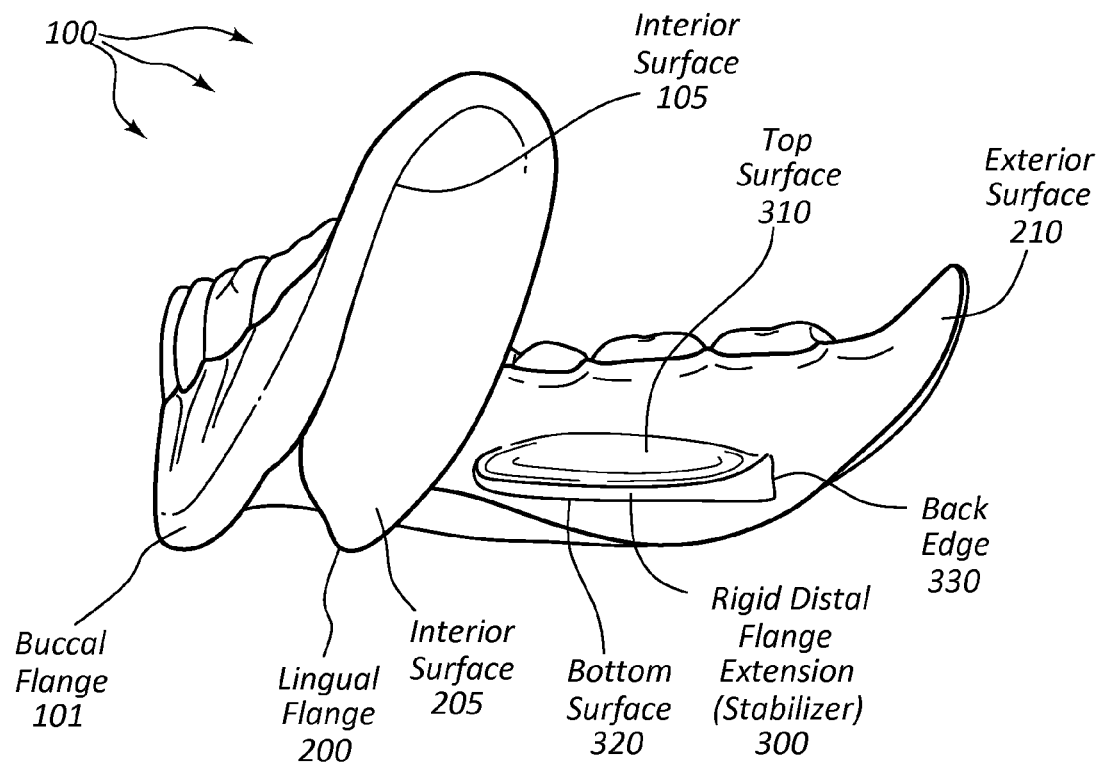
FIG. 1 depicts a perspective view of an embodiment of a stabilizer attached to a lower denture in accordance with the present disclosure.

FIG. 1 illustrates a lower denture 100 (a full lower denture). Lower denture 100 includes flanges used to stabile lower denture 100 to a mandibular bone structure. For example, buccal flange 101 and lingual flange 200 secure the lower denture 100 to gums of a patient. A rigid distal flange extension 300, hereafter referred to as a stabilizer, prevents or reduces undesired movement of lower denture 100 during mastication. Because of the stabilized and retained position of lower denture 100, equal pressures are extended along the surface area of the mandible. Thus, when stabilized, lower denture 100 can resist dislodgement and movement under load by redistributing forces across the mandibular ridge. Lower denture 100 can be secured in position by upward forces of the Genioglossus muscles and downward forces of the distal aspect of the tongue.

Buccal flange 101 has interior surface 105. Interior surface 105 is configured to make contact with one side of a patient's gums. Lingual flange 200 has interior surface 205. Interior surface 205 is configured to make contact with the other side of the patient's gums.

Stabilizer 300 is affixed to an exterior surface 210 of lingual flange 200. Stabilizer 300 includes top surface 310, bottom surface 320, and back edge 330. When lower denture 100 is positioned for use (e.g., in a patient's mouth), top surface 310 is configured to make contact with the inferior (bottom) surface (not shown) of the tongue. Also, when lower denture 100 is positioned for use, bottom surface 320 is configured to make contact with the superior (top) aspect of the Genioglossus muscle (not shown). Thus, stabilizer 300 assists with holding lower denture 100 in place by the described securing action of the tongue and the Genioglossus muscle. There is a reduction in movement of lower denture 100, thereby providing stabilization and a resulting improvement in function for lower denture 100.

In some embodiments, stabilizer 300 is coupled to the exterior surface 210 with a dental or other suitable adhesive. In other embodiments, other attachment techniques and methods can be utilized. Stabilizer 300 can be constructed of similar or even essentially the same material used to construct lower denture 100. Use of similar materials facilitates mechanical coupling, wherein the mechanical connection includes an adhesive, or chemical or mechanical bonding.

Figure 2:
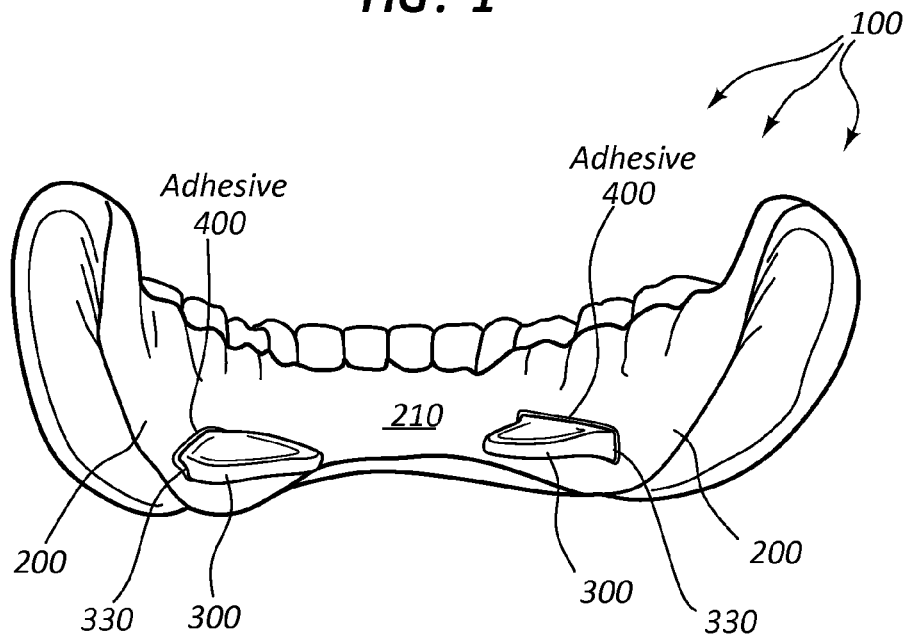
FIG. 2 is a rear view of the stabilizer embodiment as depicted in FIG. 1.

FIG. 2 illustrates another view of lower denture 100. As depicted, back edges 330 are attached to corresponding lingual flanges 200 with corresponding adhesive joints 400. In other embodiments, stabilizer 300 or a portion thereof is attached to lower denture 100. The depicted geometry and configuration of stabilizers 300 permits free movement of the Palatoglossus muscle (not shown) during swallowing and also permits free movement of the superior (top) aspects of the Genioglossus muscle and the inferior/lateral (bottom/side) aspects of the tongue. The geometry and configuration of stabilizers 300 redistributes forces across the mandibular ridge and secures the position of lower denture 100.

Figure 3:
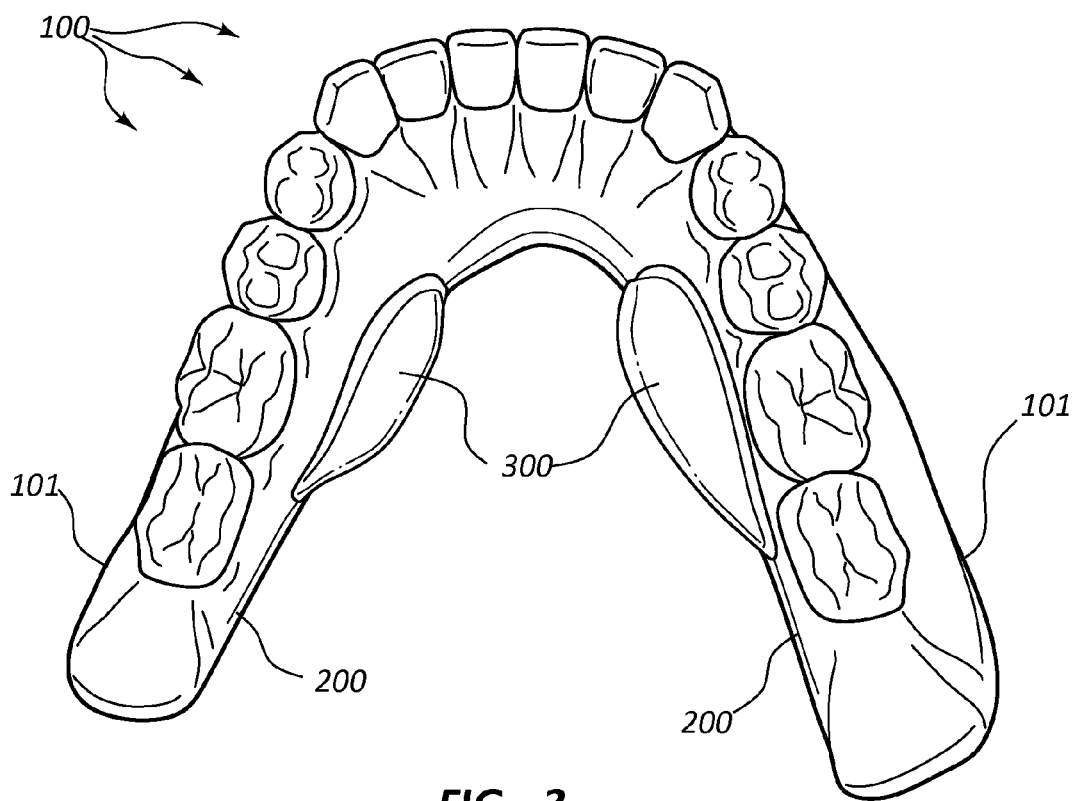
FIG. 3 is a top view of the stabilizer embodiment as depicted in FIG. 1.
Figure 4:
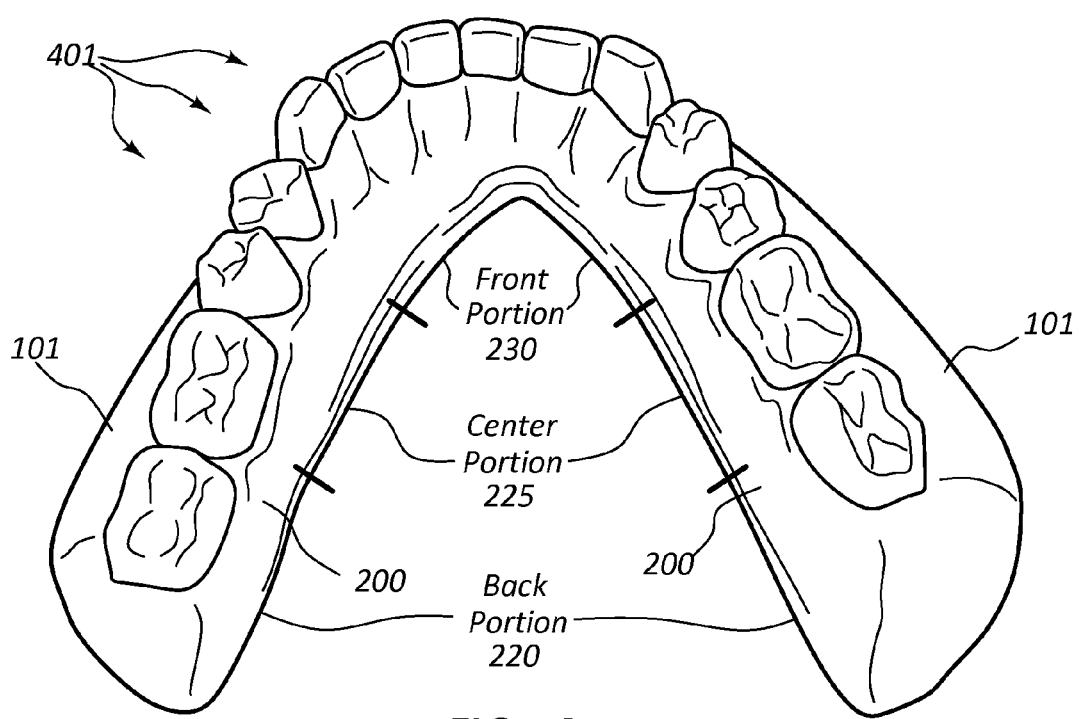
FIG. 4 is a top view of a lower denture without the stabilizer of FIG. 1.

FIG. 3 illustrates another view of lower denture 100 includes stabilizers 300. FIG. 4 illustrates a lower denture 401 without stabilizers. Thus, FIGS. 3 and 4 relative to one another depict differences between a lower denture 100 that includes stabilizers 300 and a lower denture 401 that does not include stabilizers.

As depicted, lower denture 401 also includes lingual flanges 200. On lower denture 401, stabilizers 300 or other similar stabilizers can generally be attached to lingual flange 200 at a position near center portion 225. Depending on the structure of a patient's mouth and action of mastication, the attachment position of stabilizers 300 or other similar stabilizers can be adjusted closer to front portion 230 or back portion 220 for better performance. Stabilizers 300 or other similar stabilizers can be attached above the inferior (bottom) edge of lingual flanges 200. The structure of a patient's mouth and action of mastication can also assist with determining the shape of stabilizers 300 or other similar stabilizers.

Figure 5:
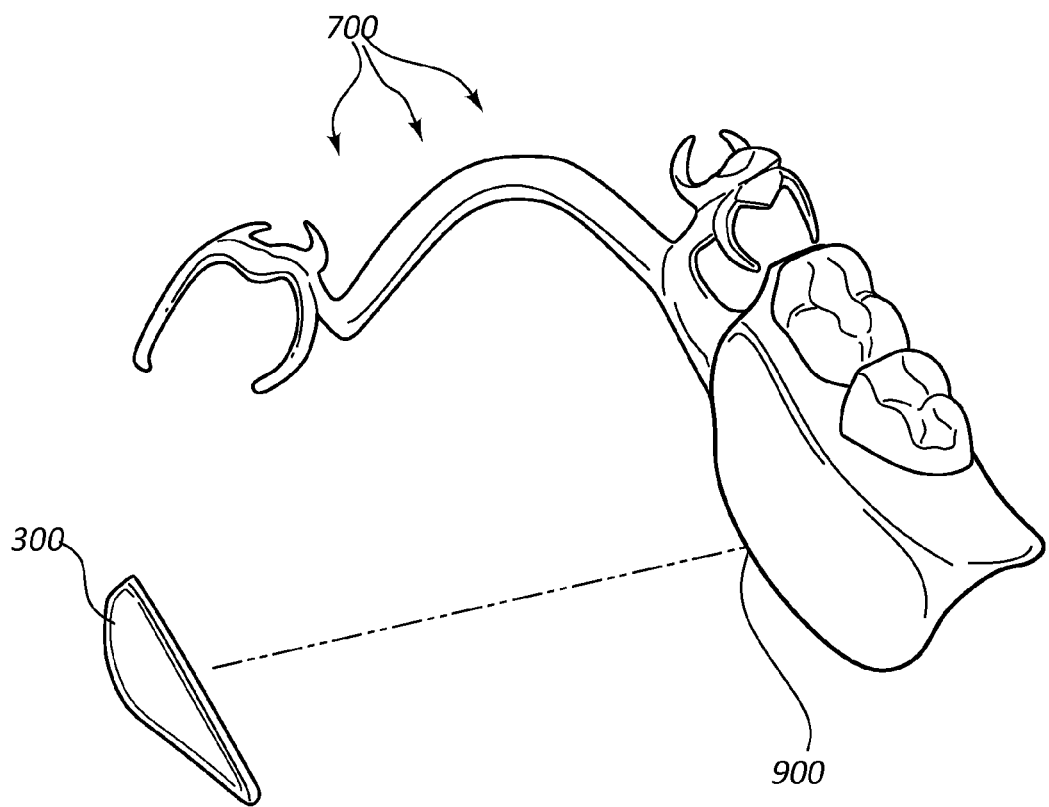
FIG. 5 depicts an embodiment of a stabilizer arrangement for a partial lower denture in accordance with the present disclosure.

In general, stabilizers can be attached to full lower dentures as well as partial lower dentures, which include lateral and bilateral dental appliances. (As depicted, FIGS. 1-3 depict stabilizers 300 attached to a full lower denture, i.e., lower denture 100). On the other hand, FIG. 5 illustrates a partial lower denture 700. As depicted, lower denture 700 includes application location 900. Stabilizer 300 can be attached to partial denture 700 (e.g., with an adhesive, chemical, or mechanical bond as described) at application location 900. Application location 900 can be selected based on the structure of a patient's mouth and action of mastication.

Figure 6:
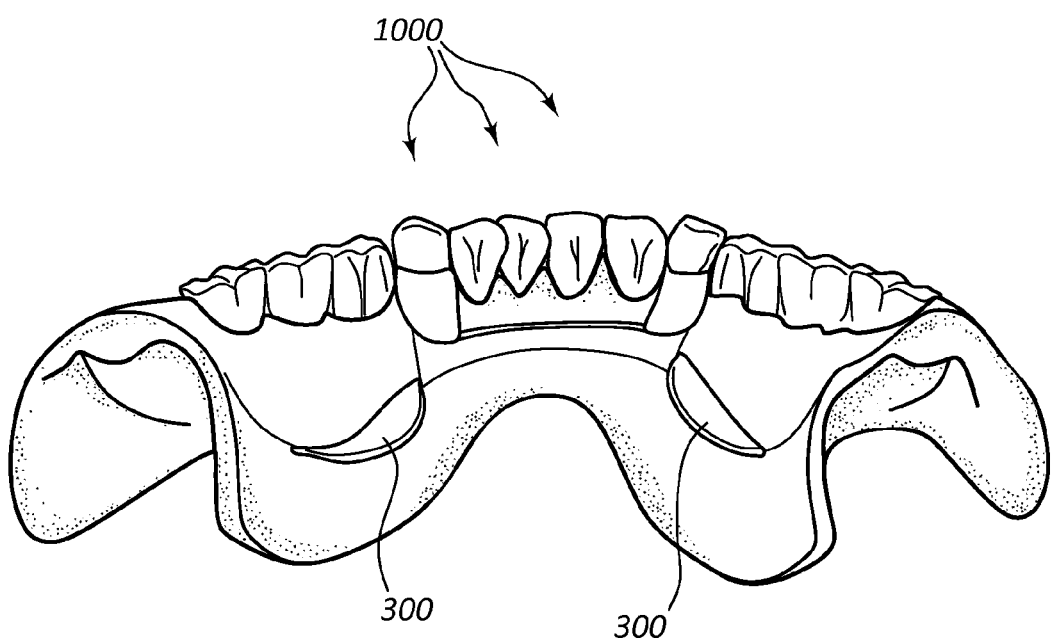
FIG. 6 depicts an embodiment of a stabilizer for a partial lower denture having saddle flanges.

FIG. 6 illustrates a partial bi-lateral, distal extension denture 1000. As depicted, stabilizers 300 are attached to saddle flanges of partial bi-lateral, distal extension denture 1000.

Figure 7:
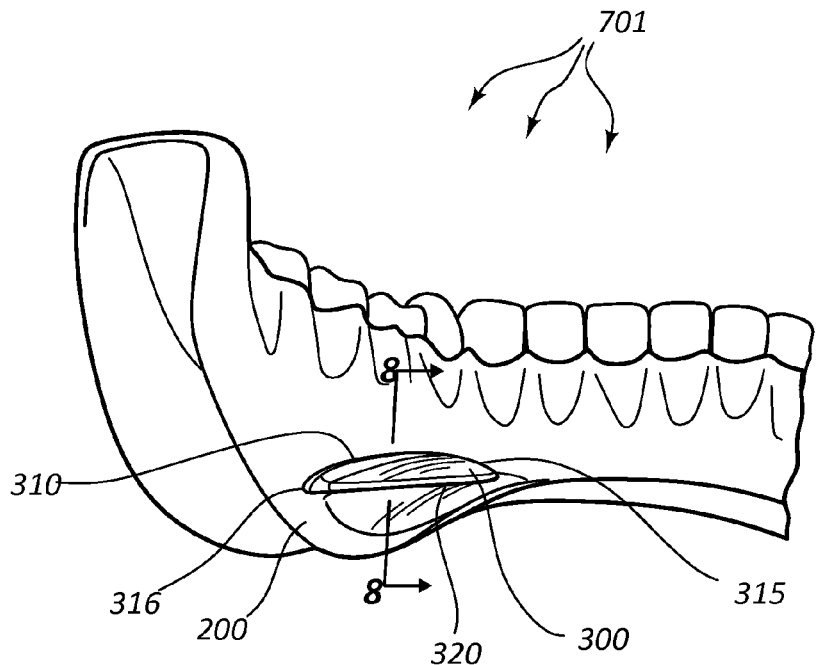
FIG. 7 depicts details of the embodiment of the stabilizer of FIG. 1.

FIG. 7 illustrates stabilizers surfaces relative to a portion of a lower denture 701. As depicted, stabilizer 300 includes a top surface 310 and bottom surface 320. Top surface 310 is configured to contact the inferior/lateral (bottom/side) of the tongue. Lower surface 320 is configured to contact the superior (top) of the Genioglossus muscle. Stabilizer 300 also includes mesial end 315 and proximal end 316. Stabilizer 300 has a tapered aspect at both mesial end 315 and proximal end 316.

Figure 8:
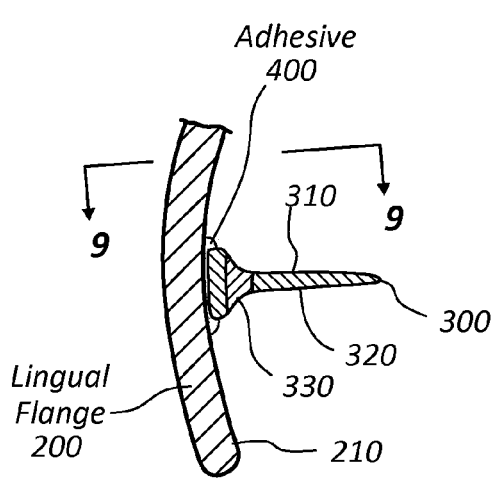
FIG. 8 is a cross sectional view of the stabilizer embodiment of FIG. 7.

FIG. 8 illustrates another view of a stabilizer 300. As depicted, stabilizer 300 includes an attachment flange 330. Adhesive 400 (or a chemical or mechanical bond) can be used to attach attachment flange 330 to exterior surface 210 of lingual flange 200. Attachment flange 330 extends essentially perpendicular from exterior surface 210 (and is also essentially perpendicular to top surface 310 and bottom surface 320) forming a T-shape in a cross section view. Attachment flange 330 provides an increase in attachment surface area for improving the structural integrity of the adhesive attachment. Other cross-section shapes and attachment methods are also possible.

Figure 9:
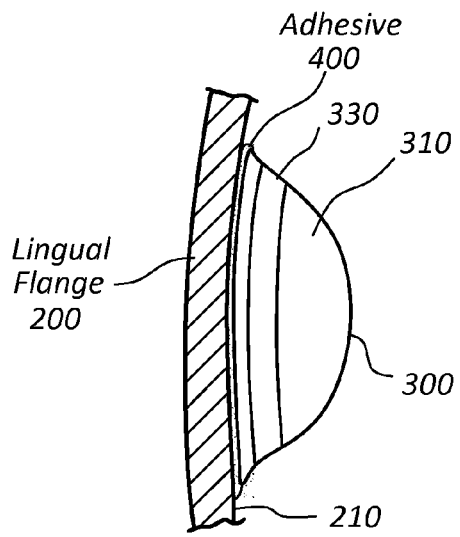
FIG. 9 depicts a top view of the cross sectional view of FIG. 8.

FIG. 9 illustrates a top view of the lingual flange 200 and stabilizer 300 from FIG. 8. In general, attachment flange 330 has a curvature that closely matches the respective curvature of the lingual flange 200.

Embodiments of the disclosure of the stabilized denture provide stability without the requirement of surgical implants or other invasive procedures. Further, embodiments may be constructed without the use of somewhat expensive metal components, such as titanium. Further, additional dental visits are typically unnecessary; and the disclosed stabilized denture may be cleaned with normal denture protocols. The cost of the described stabilizers is significantly less than the cost of implants. Further, the stabilizers do not affect the fit of the denture and may easily be removed from the denture if desired. Embodiments of the stabilized denture permit a user to chew a wider variety of foods with an increased comfort and confidence because the mandibular denture or partial denture resists movement The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed:

1. A dental appliance for insertion into a mouth of a person and resting on a mandibular bone structure, the mouth having a Genioglossus muscle and a tongue, the dental appliance comprising:
   a rigid distal flange, the rigid distal flange consisting of: a first surface, a second surface, a single continuous front edge, and a single continuous back edge, the first surface dimensioned and configured to contact a surface of a superior aspect of the Genioglossus muscle, the second surface dimensioned and configured to contact a surface of an inferior/lateral aspect of the tongue, the back edge consisting of a single mechanical connection between the back edge and a rigid lingual flange, the front edge consists of a compound curve geometry to allow a Palatoglossus muscle of the mouth free movement during swallowing and the superior aspect of the Genioglossus muscle and the inferior/lateral aspect of the tongue to move freely;
   the only connection between the rigid lingual flange and the rigid distal flange occurring along the entirety of the back edge;
   a set of rigid flanges including the rigid lingual flange and a corresponding rigid buccal flange, the set of rigid flanges conforming to the mandibular bone structure for securing the dental appliance to the mandibular bone structure, the set of rigid flanges made of denture material, the rigid lingual flange including the single mechanical connection between the back edge and the rigid lingual flange; and
   one or more artificial teeth connected to the set of rigid flanges, the one more teeth connected to the set of ridges essentially along the mandibular bone structure.

2. The dental appliance of claim 1, wherein said rigid distal flange is made of the denture material.

3. The dental appliance of claim 1, wherein the single mechanical connection uses adhesive.

4. The dental appliance of claim 1, wherein the rigid distal flange utilizes the superior aspect of the Genioglossus muscle and the inferior/lateral aspect of the tongue to retain and stabilize the dental appliance.

5. The dental application of claim 1, wherein the rigid distal flange extension is configured to redistribute forces across a mandibular ridge of the mandibular bone structure and secure the position of the dental appliance.

6. The dental appliance of claim 1, wherein the dental appliance is a full lower denture.

7. The dental appliance of claim 1, wherein the dental appliance is a partial lower denture.

8. The dental appliance of claim 7, wherein the partial lower denture includes a saddle flange.

9. The dental application of claim 1, further comprising a second rigid distal flange, the second rigid distal flange consisting of: a top surface, a bottom surface, a second single continuous front edge, and a second single continuous back edge, the bottom surface dimensioned and configured to contact a surface of a superior aspect of the Genioglossus muscle, the top surface dimensioned and configured to contact a surface of an inferior/lateral aspect of the tongue, the second back edge consisting of a further single mechanical connection between the second back edge and a rigid lingual flange;
   wherein the only connection between the rigid lingual flange and the second rigid distal flange occurs along the entirety of the second back edge;
   wherein the second front edge does not include a direct mechanical attachment to the rigid lingual flange.

10. The dental appliance of claim 1, wherein the attachment flange has a T-shaped cross section.

11. The dental appliance of claim 1, wherein the curvature of the attachment flange matches the curvature of at least a portion of the rigid lingual flange.

* * * * *